United States Patent [19]

Voss

[11] Patent Number: 4,994,066
[45] Date of Patent: Feb. 19, 1991

[54] PROSTATIC STENT

[76] Inventor: Gene A. Voss, 4227 Centergate, San Antonio, Tex. 78217

[21] Appl. No.: 255,144

[22] Filed: Oct. 7, 1988

[51] Int. Cl.⁵ ............................................. A61M 29/00
[52] U.S. Cl. .................................... 606/108; 606/191; 604/271
[58] Field of Search ............... 604/104, 264, 265, 271, 604/280, 281, 285, 174, 8; 128/341, 343, 887, DIG. 25; 608/29; 606/108, 191, 197

[56] References Cited

U.S. PATENT DOCUMENTS

| 1,039,061 | 9/1912 | Jentzsch | 128/343 |
| 2,630,805 | 3/1953 | Brehm | 128/341 |
| 3,332,424 | 7/1967 | Minteer | 604/271 |
| 3,344,791 | 10/1967 | Foderick | 604/104 |
| 3,797,478 | 3/1974 | Walsh et al. | 600/29 |
| 3,812,841 | 5/1974 | Isaacson | 600/29 |
| 3,841,304 | 10/1974 | Jones | 600/29 |
| 4,142,516 | 3/1979 | Adair | 604/280 |
| 4,434,797 | 3/1984 | Silander | 604/264 |
| 4,531,933 | 7/1985 | Norton et al. | 604/281 |
| 4,710,169 | 12/1987 | Christopher | 604/104 |
| 4,762,128 | 8/1988 | Rosenbluth | 604/96 |

FOREIGN PATENT DOCUMENTS

| 0448678 | 8/1927 | Fed. Rep. of Germany | 128/341 |
| 0586018 | 12/1924 | France | 604/104 |

Primary Examiner—John D. Yasko
Assistant Examiner—Anthony M. Gutowski
Attorney, Agent, or Firm—David G. Henry

[57] ABSTRACT

A stent useful for treatment of prostatic urethral hypertrophy having a cylindrical conduit with a conical flange on one end and an annular flange on the other. The stent is constructed of a medical grade elastomer whereby it may be compressed for implantation and can thereafter be left in place for extended periods of time without adverse reactions by the patient. The stent is placed with a constructed endoscope with a novel everted, tubular retaining member to hold the stent in place during the implantation procedure.

10 Claims, 2 Drawing Sheets

PROSTATIC STENT

BACKGROUND OF THE INVENTION

1. Field of the Invention

The present invention generally relates to medical devices used to expand tubular membranes. More particularly, the present invention is designed to mitigate prostatic hypertrophy by the use of a semi-permanent stent.

2. Background Information

Many vessels in the human body have a tendency to become obstructed or constricted after a period of years, causing severe side affects. For example, arteriosclerosis, or hardening of the arteries, is a result of a buildup of placque on the inner walls of the coronary arteries, leading to reduced blood flow and oxygen intake by the cardiac muscle. The present invention is directed to a device designed to mitigate or alleviate such constriction in any one of several ducts and vessels of the body. Actually, the present invention was originally developed in order to diminish the effects of prostatic hypertrophy.

The prostate gland is located next to the inner wall of the rectum, around the urethra and directly below the bladder. If the prostate becomes swollen, due to infection or some disease, it will crowd the urethra and cause discomfort. Typically, as a man nears fifty years of age, the gland begins to grow in size, apparently due to hormonal changes. This is enlargement is known as benign prostatic hypertrophy, or BPH. Sixty percent of men over 60 have BPH, and nearly 95% of men over 80 suffer from this condition. The enlargement of the glandular tissue within the prostatic capsule can cause not only minor trouble, such as nocturia (waking up at night to urinate) or overflow incontinence, but can further lead to uremia (excess urea in the blood), renal failure, and even death.

BPH is not a recent disease of the twentieth century, and some treatments have been known for literally thousands of years. The ancient Egyptians knew of prostatic enlargement, and inserted reeds, or copper or silver tubes through the penis and urethra to widen the urinary passage in the gland. Benjamin Franklin has been credited with inventing a urethral catheter for use by his brother, a victim of prostatic obstruction.

Catheters are used today to ease acute retention of urine brought about by BPH. The most common of these is the Foley catheter developed by Dr. Frederick Foley. The Foley catheter is, however, at best a temporary measure providing only transitory relief. Prostatic massage can also provide temporary relief in cases where BPH is accompanied by congestion of the thirty to fifty tubes or saclike ducts within the prostate gland, but this usually only postpones surgery. For permanent relief of the condition, some form of surgery is generally required. Administration of female hormones will diminish the disorder, but the side effects of this treatment make it most undesirable.

Presently, there are four different surgical procedures available to remove all or part of the prostate gland. The first of these is transurethral resection (TUR). In this procedure, a stiff, hollow sheath is first inserted into the penile urethra, and then a fiber optic instrument similar to a cystoscope, known as a resectoscope, it passed through the sheath to the prostate area. A looped piece of wire carrying an electrical current is moved back and forth, cutting away excess prostatic tissue. An indwelling drainage catheter, such as those shown in U.S Pat. No. 3,394,705 issued to D. Abramson, and U.S. Pat. No. 4,571,241 issued to T. Christopher, is left in the urethra and bladder for twenty-four hours after the operation.

The problem with TUR's is that, if the prostate has grown to a relatively large size, the patient will probably need another surgical procedure. This is highly undesirable since most men are already fairly old when they have a TUR, and will likely be less healthy when the procedure is repeated. Where a large amount of the prostate is removed, two other techniques may be used: suprapubic and retropubic prostatectomies.

In a suprapubic prostatectomy, an incision is made between the navel and the pubic bone. The incision is typically four to six inches long. An incision is further made in the bladder itself, and the prostate gland is then removed. In the retropubic prostatectomy, the same initial incision is made, but the bladder is left undisturbed. Rather, the intestines are pushed away from the bladder, and the fibrous capsule surrounding the prostate gland is severed. All or some of the gland is then removed.

The fourth procedure is known as a perineal prostatectomy. In this technique, an incision is made through the perineum, between the anus and scrotum. This provides a more direct route to the gland, but it can have several undesirable consequences, including impotency due to severed nerves. All three of the prostatectomies are basically unappealing as they introduce all of the complications of open surgery.

One final method of cryosurgery has been recently attempted with uncertain results. In that method, a probe containing liquid nitrogen is inserted into the urethra, shrinking away swollen tissue. Physicians are expectedly cautious in discussing the merits of this procedure.

Along another vein, physicians have created several different catheters designed to dilate stenoses or occlusions in a body passageway. For example, U.S. Pat. No. 4,493,711 issued to Chin et al. is directed to a extrusion catheter providing means for placement of a soft tube through the lumen of an occluded artery or vein. Several dilation catheters were designed for coronary angioplasty; these include: U.S. Pat. No. 4,413,989 issued to Schjeldahl et al.; U.S. Pat. No. 4,315,512 issued to Fogarty; and U.S. Pat. No. 4,195,637 issued to Gruntzig et al. It would be possible to utilize such catheters in BPH patients, but the catheters only temporarily expand the prostatic urethra, and the enlarged prostate will nearly immediately return to its collapsed position.

It would, therefore, be desirable and advantageous to devise a dilation stent which could be permanently placed in the prostatic urethra to relieve benign prostatic hypertrophy. The inventor knows of no such stent which, once in place, could expand to enlarge the urethra. Such a stent could also be used for other ducts and vessels in the body. There is one variable diameter catheter, disclosed in U.S. Pat. No. 4,601,713 issued to C Fuqua, that may be longitudinally folded for insertion into the urethra and then unfolded after insertion for transporting a fluid therein, but that catheter is also a temporary device in which one end of the catheter exits the body for access to an external source of fluids. Also, no catheter or stent can be placed in a body orifice in a permanent fashion, and yet be later removed should complications arise.

SUMMARY OF THE INVENTION

Accordingly, the primary object of the present invention is to provide a stent capable of indefinitely residing in a prostatic urethra.

Another object of the invention is to provide means and a method for the insertion and removal of such a stent.

Yet another object of the invention is to provide a prostatic stent for relieving benign prostatic hypertrophy.

The foregoing objects are achieved in a stent having a cylindrical conduit with a conical flange on one end and an annular flange on the other. The stent is constructed of a medical grade elastomer whereby it can be compressed for implantation and can thereafter be left in place for extended periods of time without adverse reactions by the patient.

The stent is placed with a specially adapted endoscope with a novel everted, tubular retaining member to hold the stent in place during the implantation procedure.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

DESCRIPTION OF THE PREFERRED EMBODIMENTS

Figure 1:
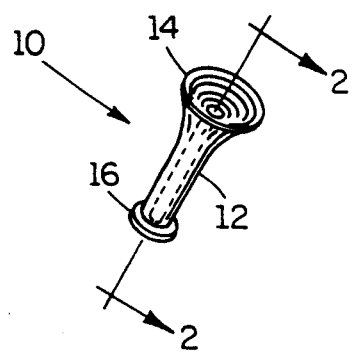
FIG. 1 is a perspective view of the stent of applicant's invention.

Referring to FIG. 1, applicant's stent 10 comprises a cylindrical conduit 12 having a first (proximal) end and a second (distal) end. A conically shaped flange 14 is formed at the first end. An annularly shaped flange 16 is formed at the second end.

Figure 2:
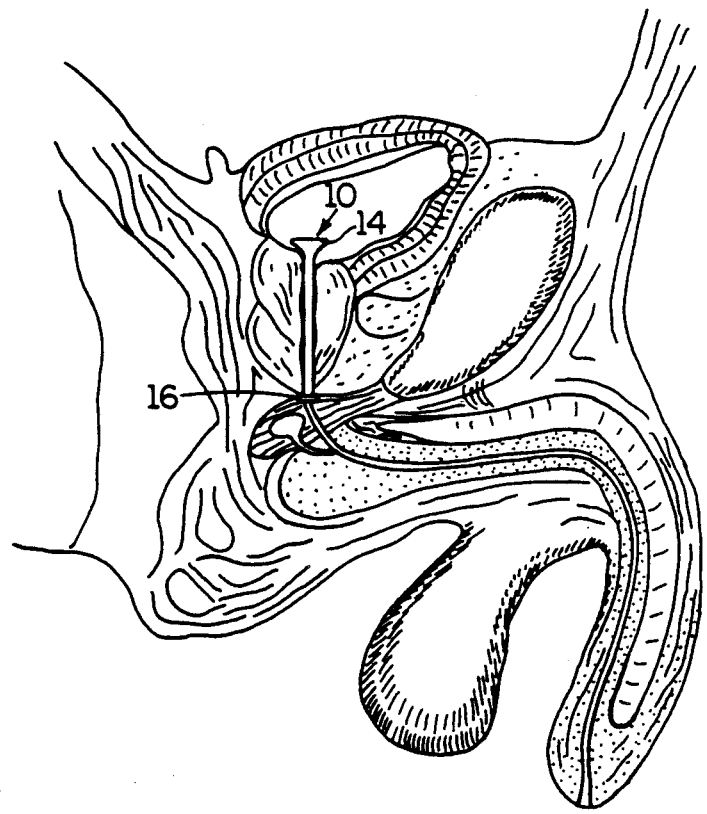
FIG. 2 is an anatomical drawing showing the stent of applicant's invention in proper position within the prostatic urethra.

Referring to FIG. 2, when in place, the conduit 12 of the properly implanted stent 10 of appropriate dimensions will extend through and be substantially coextensive with the prostatic portion of the urethra. The conical flange 14 will extend from the conduit 12 in the prostatic urethra into and conforming to the neck of the bladder. At the same time, the annular flange 16 will be situated just beyond the prostatic urethra in the membranous portion of the urethra. In this way, the annular flange 16 will abut the internal urethral protrusions defined by the prostate lobes' impingement on the urethra. The annular flange 16 and the conical flange 14 thereby serve, in concert, to secure the stent 10 from significant longitudinal shifting within the urethra.

The conical shape of the first end's flange is critical in the design of the stent. This design allows complete drainage of the bladder while still providing a proximal anchor for the stent 10 and reducing the chance of trauma to urethral epithelium at the neck of the bladder.

It is clear that the stent 10 design including the conical flange 14 is optimal. If the stent 10 were to have an annular rather than conical like that at the stent's first end, such annular flange 16 would provide an undesirably localized point of pressure on the urethral epithelium at the point of constriction by the prostate. This would tend to cause trauma and/or localized ischemia to the urethral epithelium. By comparison, the annular flange 16 is most appropriate at the second end of the stent, in part, because there is no significant external compression of the urethra in the membranous portion where the annular flange 16 resides. Also, the structure of the membranous portion of the urethra is not such to accommodate a conical flange. The membranous portion of the urethra easily accommodates the annular flange.

Figure 3:
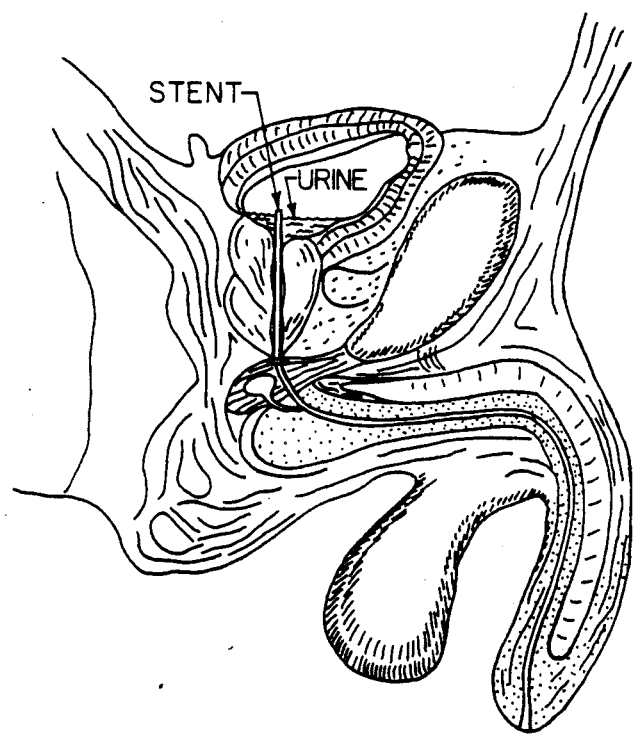
FIG. 3 is an anatomical drawing showing a stent which lacks a conical flange and extends into the bladder and the resulting collection of urine around the stent near the neck of the bladder.
Figure 4:
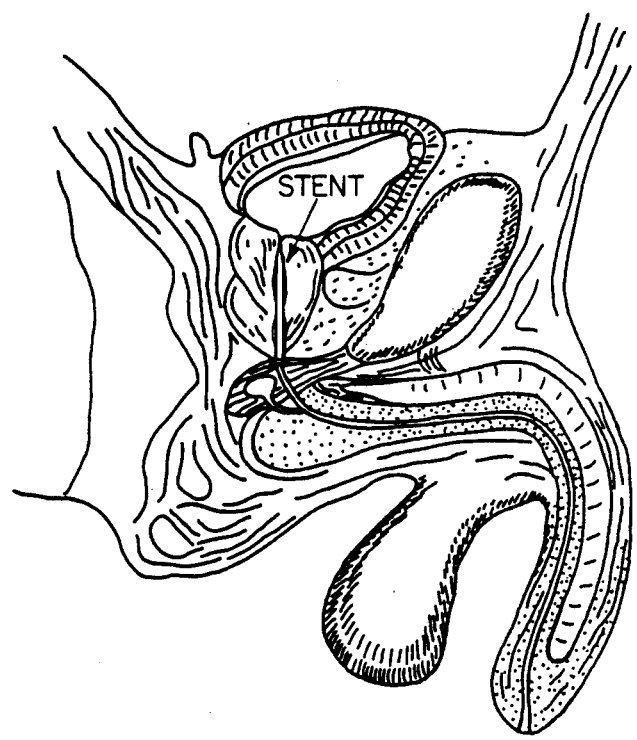
FIG. 4 is an anatomical drawing showing a stent which lacks a conical flange and which does not extend beyond the prostatic urethra and the resulting obstruction of the stent's end nearest the bladder.

Referring to FIGS. 3 and 4 Equally unacceptable as an annular flange 16 on the first end is the complete absence of a flange on the first end. The lack of a flange on the first end would allow the stent 10 to shift in a direction away from the bladder. This would be particularly troublesome at the end of the implantation procedure (to be discussed hereinafter) when instruments used to place the stent 10 are withdrawn and the stent 10 would tend to follow the instruments.

Referring to FIGS. 3 and 4, an equally deleterious effect of having no flange at the stent's first end would be either to prevent full evacuation of the bladder if the conduit 12 extended well into the bladder or to thwart the function of the stent 10 by way of the urethra simply closing around the end of the conduit 12 to seal it shut. These latter two problems are depicted respectively by FIGS. 3 and 4. Collection of trapped urine around the conduit 12 near the neck of the bladder would invite bacterial infection.

Figure 5:
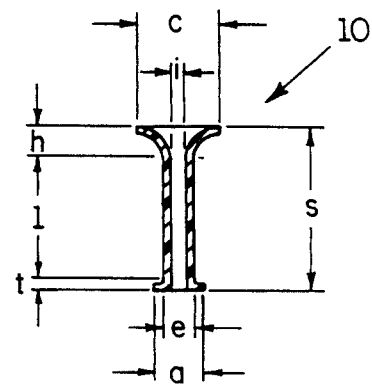
FIG. 5 is a cross sectional view of the stent of applicant's invention with dimensional reference characters cited in the specification.

Referring to FIG. 5, stents made according to applicant's invention will vary in size to accommodate the full spectrum of possible patient physiology. Whatever the actual dimensions, the ratios of the stent length (s) to conduit length (1), to interior conduit diameter (i), to exterior conduit diameter (e), to conical flange base diameter (c), to conical flange height (h), to annular flange thickness (t) and to annular flange diameter (a), will remain virtually constant. Accordingly, the following formulae will approximate the appropriate relative dimensions of applicant's stent:

$l = .90(s)$
$i = .15(s)$,
$e = .20(s)$,
$c = .50(s)$,
$h = .12(s)$.
$t = .05(s)$.
$a = .35(s)$.

The properties of the material used to construct the stent 10 are very important to its function. Because the course of the prostatic urethra varies from patient to patient, the stent 10 should be capable of readily conforming to the path of the urethra without forcibly impinging on the urethral wall causing epithelial trauma and/or ischemia. Accordingly, the preferred embodiment of applicant's stent 10 is made of a medical grade silicon elastomer material such as "SILASTIC." ("SILASTIC" is a registered trademark of Dow Corning Corporation). The thickness of the material of the conduit 12 portion of the stent 10 (as indicated above) when made from such a substance gives the stent 10 the necessary flexibility.

It is anticipated that the preferred method of manufacturing the stent 10 will involve making appropriate molds and forming the stents by injection molding.

To permit implantation of the stent 10 to be monitored by fluoroscopic means, a radiopaque material may be either applied to the external surfaces of the stent 10 or may be incorporated into the material forming the stent 10 before the stent 10 is molded. Suitable radiopaque materials are known in the art and will not be set out in detail herein.

Figure 6:
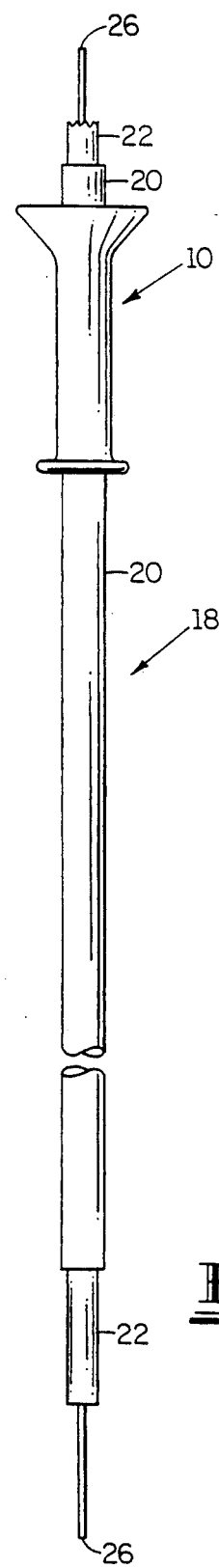
FIG. 6 is an elevational view of the endoscope of applicant's invention with the stent placed thereon, but with the internal tube not positioned for securing the stent for implantation.
Figure 7:
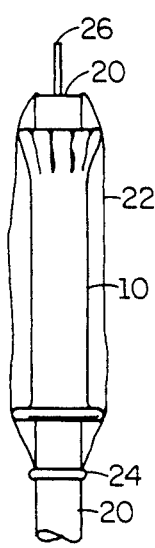
FIG. 7 is an elevational view of the stent end of the endoscope wherein the internal tube is everted over the stent thereby compressing and securing the stent for implantation.

Referring to FIGS. 6 and 7, implantation of the stent 10 is accomplished using a specially adapted endoscope 18. The endoscope 18 of applicant's invention includes a flexible plastic external tube 20 (of a medical grade plastic like that used for applicators for standard urinary catheters). The external tube 20 has a small exterior annular flange 21 formed approximately 1.5 inches from the insertion end. As the endoscope with stent 10 thereon for implantation is assembled, the external tube 20 is inserted through the conduit 12 of the stent 10 and the stent's annular flange 16 is seated against the tube's external flange 21. The scope's flange 21 serves to prevent the stent 10 from shifting backwards on the external tube 20 during inward movement of the endoscope 18 during implantation.

Referring particularly to FIG. 7, a smaller, coaxially situated internal tube 22 passes through the external tube 20 and serves to hold the stent 10 in a compact arrangement for traversing the urethral path and, as will be shown, for releasing the stent 10 once in position. The internal tube 22 is made from a highly flexible, resilient, and slightly elastic material which must also be appropriate for medical use. At the insertion end of the internal tube 22, the internal tube 22 is turned back over the external tube 20 with the stent 10 situated thereon and the end of the internal tube 22 is secured on the outer surface of the external tube 20 by a clamp ring 24. A fiber-optic scope 26 extends through the interior of internal tube 22 to allow visual guidance during implantation.

The basic procedures involved in, and the path to be taken in guiding the stent 10 into a patient and to its proper position are not substantially different from that involved with placing a standard urinary catheter and will not, therefore, be discussed here.

Once the stent 10 has been positioned with the conical flange 14 extending into the neck of the bladder, a traction force is applied on the external end of the internal tube 22 to break it from the clamp ring 24 and to pull the internal tube 22 over the stent 10 surface and ultimately into the interior of the external tube 20. By this operation, the conical flange 14 is released and anchors the stent 10 within the bladder. The external tube 20 may then be retracted leaving the stent 10 in position.

The clamp ring 24 should be designed to hold a portion of the internal tube 22 snugly, but should allow the internal tube's 22 end to slip from the ring 24 without breaking in response to a moderate traction force. In the alternative, a medically appropriate cement may be used to affix the internal tube 22 to the external tube 20 so long as the bond is such that the internal tube 22 may be retracted without a substantial force being applied.

To assure ease of procedure and to minimize trauma to the urethral epithelium by erratic movement, particularly when retracting the external tube 20, the surfaces of the external tube 20, interior tube 22, and the stent 10 may be coated with TEFLON (TEFLON is a registered trademark of DuPont Chemical Corporation). This allows the internal tube 22 to move smoothly within the exterior tube 20 and over the stent 10 during retraction of internal tube 22 and release of the stent 10. This also facilitates movement of the stent 10 from the external tube 20 once the stent 10 is properly positioned and during retraction of the external tube 20.

Although the invention has been described with reference to specific embodiments, this description is not meant to be construed in a limiting sense. Various modifications of the disclosed embodiment, as well as alternative embodiments of the invention will become apparent to persons skilled in the art upon reference to the description of the invention. It is therefore contemplated that the appended claims will cover such modifications that fall within the true scope of the invention.

I claim:

1. A stent for symptomatic treatment of prostatic hypertrophy comprising:
   a cylindrical conduit having first and second conduit ends, an interior annular surface, and an exterior annular surface;
   a conical flange radiating outwardly from said conduit's said exterior annular surface at said first conduit end; and
   an externally situated, coaxial, annular flange at said second conduit end;
   said stent being constructed of a medical grade plastic material suitable for surgical implantation in humans;
   said stent being associated with implantation means comprising:
   a first tube having a first tube insertion end and a first tube external end, a first tube annular flange being formed on said first tube at a distance from said insertion end slightly greater than the overall axial length of said stent, said first tube having an external diameter approximately equal to, but no greater than the internal diameter of said conduit, said insertion end of said first tube extending through said conduit whereby said stent annular flange at said first end of said stent is juxtaposed against said first tube annular flange and said conical flange of said stent is adjacent to said insertion end, said first tube being made of a medical grade plastic material suitably flexible for traversing the urethral path of said patient; and
   a second tube extending through the interior of said first tube, said second tube having a second tube insertion end and a second tube external end, said second tube being formed from a highly flexible medical grade plastic material, said second tube insertion end of said second tube being turned back over said first tube insertion end and enveloping said stent situated thereon, the terminus of said second tube insertion end being affixed to the exterior surface of said first tube adjacent to said first tube annular flange opposite said stent by securing means, said second tube external end extending beyond said first tube external end whereby said second tube external end may be grasped and a traction force applied to retract said second tube dislodging said second tube insertion end from said securing means, said second tube being sized at said second tube insertion end whereby said conical flange is held compactly for traversing said urethral path.

2. The invention of claim 1 further comprising fiber optic scope means extending through the interior of said second tube beyond said first tube insertion end suitable for connection to fiber optic viewing means whereby said traversing of said urethral path and implantation of said stent may be visually monitored.

3. The invention of claim 1 further comprising a radiopaque material adhered to said plastic material forming said stent.

4. A stent for symptomatic treatment of prostatic hypertrophy comprising
   a cylindrical conduit having first and second conduit ends, an interior annular surface, and an exterior annular surface;
   a conical flange radiating outwardly from said conduit's said exterior annular surface at said first conduit end; and
   an externally situated, coaxial, annular flange at said second conduit end;
   said stent being constructed of a medical grade plastic material suitable for surgical implantation in humans;
   said stent being associated with implantation means comprising:
      a first tube having a first tube insertion end and a first tube external end, a first tube annular flange being formed on said first tube at a distance from said insertion end slightly greater than the overall axial length of said stent, said first tube having an external diameter approximately equal to, but no greater than the internal diameter of said conduit, said insertion end of said first tube extending through said conduit whereby said stent annular flange at said first end of said stent is juxtaposed against said first tube annular flange and said conical flange of said stent is adjacent to said insertion end, said first tube being made of a medical grade plastic material suitably flexible for traversing the urethral path of said patient; and
      a second tube extending through the interior of said first tube, said second tube having a second tube insertion end and a second tube external end, said second tube being formed from a highly flexible medical grade plastic material, said second tube insertion end of said second tube being turned back over said first tube insertion end and enveloping said stent situated thereon, the terminus of said second tube insertion end being affixed to the exterior surface of said first tube adjacent to said first tube annular flange opposite said stent by securing means, said second tube external end extending beyond said first tube external end whereby said second tube external end may be grasped and a traction force applied to retract said second tube dislodging said second tube insertion end from said securing means, said second tube being sized at said second tube insertion end whereby said conical flange is held compactly for traversing said urethral path;
   the overall longitudinal, axial length of said conduit being such that said conduit may extend through the prostatic urethra of a human male patient while said conical flange at said first end of said conduit extends into said patient's bladder while contacting and generally conforming to the neck of said patient's bladder, and said annular flange concurrently resides in said the membranous portion of said patient's urethra closely adjacent to said prostatic urethra.

5. The invention of claim 4 further comprising a radiopaque material incorporated into said plastic material forming said stent.

6. A stent for symptomatic treatment of prostatic hypertrophy comprising:
   a cylindrical conduit having first and second conduit ends, an interior annular surface, and an exterior annular surface;
   a conical flange radiating outwardly from said conduit's said exterior annular surface at said first conduit end; and
   an externally situated, coaxial, annular flange at said second conduit end;
   said stent being constructed of a medical grade plastic material suitable for surgical implantation in humans, the overall longitudinal, axial length of said conduit is such that said conduit may extend through the prostatic urethra of a human male patient while said conical flange at said first end of said conduit extends into said patient's bladder while contacting and generally conforming to the neck of said patient's bladder, and said annular flange concurrently resides in said the membranous portion of said patient's urethra closely adjacent to said prostatic urethra, said conduit having an external diameter approximately .20 times the overall longitudinal, axial length of said stent and said conical flange has a base radius no less than approximately .50 times said length of said stent and a height approximately .20 times said length of said stent as measured parallel with the longitudinal axis of said conduit from the terminus of said first conduit end; and
   implantation means, said implantation means comprising:
      a first tube having a first tube insertion end and a first tube external end, a first tube annular flange being formed on said first tube at a distance from said insertion end slightly greater than the overall axial length of said, stent, said first tube having an external diameter approximately equal to, but no greater than the internal diameter of said conduit said insertion end of said first tube extending through said conduit whereby said stent annular flange at said first end of said stent is juxtaposed against said first tube annular flange and said conical flange of said stent is adjacent to said insertion end, said first tube being made of a medical grade plastic material suitably flexible for traversing the urethral path of said patient; and
      a second tube extending through the interior of said first tube, said second tube having a second tube insertion end and a second tube external end, said second tube being formed from a highly flexible medical grade plastic material, said second tube insertion end of said second tube being turned back over said first tube insertion end and enveloping said stent situated thereon, the terminus of said second tube insertion end being affixed to the exterior surface of said first tube adjacent to said first tube annular flange opposite said stent by securing means, said second tube external end extending beyond said first tube external end whereby said second tube external end may be grasped and a traction force applied to retract said second tube dislodging said second tube insertion end from said securing means, said second tube being sized at said second tube insertion end whereby said conical flange is held compactly for traversing said urethral path; and fiber optic scope means extending through the interior of said second tube beyond said first tube insertion end suitable for connection to fiber optic viewing means whereby said traversing of said urethral path and implantation of said stent may be visually monitored.

7. A method of providing symptomatic treatment of benign prostatic hypertrophy of a human male patient comprising the steps of:

selecting a stent for implantation in said patient's urethra, said stent comprising:

a cylindrical conduit having first and second conduit ends, an interior annular surface, and an exterior annular surface;

a conical flange radiating outwardly from said conduit's said exterior annular surface at said first conduit end; and an externally situated, coaxial, annular flange at said second conduit end;

said stent being constructed of a medical grade plastic material suitable for surgical implantation in humans;

said conduit of said stent having an overall longitudinal, axial length such that said conduit may extend through the prostatic urethra of said patient while said conical flange at said first conduit end extends into said patient's bladder at the neck of said bladder and said annular flange resides in said patient's membranous urethra closely adjacent to said prostatic urethra; and implanting said stent in said patient whereby said conduit extends through the prostatic urethra of said patient, said conical flange extends into said patient's bladder at said neck of said bladder and said annular flange resides in said patient's membranous urethra closely adjacent to said prostatic urethra;

said stent being associated with implantation means for use in implanting said stent comprising:

a first tube having a first tube insertion end and a first tube external end, a first tube annular flange being formed on said first tube at a distance from said insertion end slightly greater than the overall axial length of said stent, said first tube having an external diameter approximately equal to, but no greater than the internal diameter of said conduit, said insertion end of said fist tube extending through said conduit whereby said stent annular flange at said first end of said stent is juxtaposed against said first tube annular flange and said conical flange of said stent is adjacent to said insertion end, said first tube being made of a medical grade plastic material suitable flexible for traversing the urethral path of said patient; and a second tube extending through the interior of said first tube, said second tube having a second tube insertion end and a second tube external end, said second tube being formed from a highly flexible medical grade plastic material, said second tube insertion end of said second tube being turned back over said first tube insertion end and enveloping said stent situated thereon, the terminus of said second tube insertion end being affixed to the exterior surface of said first tube adjacent to said first tube annular flange opposite said stent by securing means, said second tube external end extending beyond said first tube external end whereby said second tube external end may be grasped and a traction force applied to retract said second tube dislodging said second tube insertion end from said securing means, said second tube being sized at said second tube insertion end whereby said conical flange is held compactly for traversing said urethral path; and said stent being implanted by directing said implantation means through said patient's urethra until said conical flange of said stent extends into the neck of said patient's bladder, applying a traction force to said second tube at said second tube external end thereby releasing said stent and allowing said conical flange to unfold, and retracting said first and second tubes from said patient.

8. The method of claim 7 wherein the overall longitudinal, axial length of said conduit is such that said conduit may extend through the prostatic urethra of a human male patient while said conical flange at said first end of said conduit extends into said patient's bladder while contacting and generally conforming to the shape of the neck of said patient's bladder, and said annular flange concurrently resides in said the membranous portion of said patient's urethra closely adjacent to said prostatic urethra.

9. The method of claim 7 wherein said implantation means further comprises fiber optic viewing means extending through said second tube beyond said first tube insertion end and wherein the progress of said implantation is monitored visually using said viewing means.

10. The method of claim 7 wherein said implantation comprises a rediopaque material whereby progress of said stent through said patient's urethra during said implantation may be monitored by fluoroscopic viewing means.

* * * * *